US00PP10831P

United States Patent [19]

Bottoms et al.

[11] Patent Number: Plant 10,831

[45] Date of Patent: Mar. 16, 1999

[54] SCHEFFLERA PLANT NAMED 'PVN II VARIEGATED'

[75] Inventors: Ellsworth D. Bottoms; Luseane Bottoms, both of Apopka, Fla.

[73] Assignee: Pine Valley Nursery, Inc., Apopka, Fla.

[21] Appl. No.: 932,199

[22] Filed: Sep. 17, 1997

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 6,134 3/1988 Gorvel ..... Plt./88.1

P.P. 8,198 4/1993 Gorvel ..... Plt./88.1

P.P. 9,955 7/1997 Bottoms et al. ..... Plt./88.1

*Primary Examiner*—Howard J. Locker

*Assistant Examiner*—Kent L. Bell

*Attorney, Agent, or Firm*—C. A. Whealy

[57] ABSTRACT

A distinct cultivar of Schefflera plant named 'PVN II Variegated', characterized by its very compact plant habit; moderate vigor; dense and full appearance; small leaves; and glossy, dark green leaflets with variable yellowish green to ivory variegation patterns that may be centrally or marginally located.

1 Drawing Sheet

The present invention relates to a new and distinct cultivar of Schefflera plant, botanically known as *Schefflera arboricola,* and hereinafter referred to by the cultivar name 'PVN II Variegated'.

The new cultivar was discovered by the inventors in a controlled environment in Apopka, Fla., in April, 1995, as a naturally-occurring mutation of the *Schefflera arboricola* cultivar 'PVN-1' (disclosed in U.S. Plant Pat. No. 9,955). The new cultivar was observed as a single plant in a group of plants of the parent cultivar. The selection of this plant was based on its yellowish green to ivory leaf variegation compared to the nonvariegated leaves of the parent cultivar. Similar to the parent cultivar, plants of the new Schefflera are much more compact than other commercially-available *Schefflera arboricola* cultivars.

Asexual propagation of the new cultivar by terminal cuttings taken in a controlled environment in Apopka, Fla., has shown that the unique features of this new Schefflera are stable and reproduced true to type in successive generations.

The new Schefflera has not been observed under all possible environmental conditions. The phenotype may vary somewhat with variations in environment such as temperature and light intensity, without, however, any variance in genotype.

The following traits have been repeatedly observed and are determined to be the unique characteristics of plants of the new Schefflera. These characteristics in combination distinguish the new Schefflera as a new and distinct cultivar:

1. Very compact plant habit.
2. Moderate vigor.
3. Closely-spaced leaves and short petioles which give a dense and full appearance.
4. Relatively small leaflets.
5. Glossy, dark green leaflets with variable yellowish green to ivory variegation patterns that may be centrally or marginally located.

BRIEF DESCRIPTION OF THE PHOTOGRAPHS

The accompanying colored photographs illustrate the overall appearance of the new Schefflera, showing the colors as true as it is reasonably possible to obtain in colored reproductions of this type.

The top photograph comprises a top perspective view of a typical potted plant of the new Schefflera.

The lower photograph comprises a close-up view of typical leaves of the new Schefflera. Leaf colors in the photographs may differ from actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Apopka, Fla., during the spring and summer under commercial practice in a polypropylene-covered shadehouse that provided a 60% reduction of the ambient light level. Average day and night temperatures were 30° and 16° C., respectively.

Botanical classification: *Scheffera arboricola* cultivar 'PVN II Variegated'.

Parentage: Naturally-occurring mutation of *Schefflera arboricola* cultivar 'PVN-1', disclosed in U.S. Plant Pat. No. 9,955.

Propagation: By terminal cuttings.

*Time to initiate roots.*—Winter: About 35 days at 16° C. Summer: About 21 days at 30° C.

*Time to develop roots.*—Winter: About 48 days at 10° to 16° C. Summer: About 35 days at 30° to 32° C.

*Rooting habit.*—Numerous, fleshy and thick.

Plant description:

*Plant shape.*—Mostly erect and upright, inverted triangle, symmetrical.

*Growth habit.*—Very compact, appropriate for 10 to 15-cm containers. Bushy, dense and full. Removal of terminal apices enhances branching.

*Plant height.*—About 34 cm from soil level to top of leaf plane.

*Plant width.*—About 48 cm.

*Plant vigor.*—Moderate vigor.

*Stem description.*—Internode length: About 1 cm. Color: Young: 144A. Mature: 145A to 150D.

*Foliage description.*—Radially compound leaves. Number of leaflets per leaf: Usually about eight. Leaf diameter: About 7.5 cm. Leaflet shape: Oblong. Leaflet length: About 4 cm. Leaflet width: About 1.5 cm. Margin: Entire. Leaflet tip: Rounded. Leaflet base: Cuneate. Leaflet aspect: Flat to undulate. Leaflets with larger areas of variegation are more undulate than leaflets with smaller or no areas of variegation. Leaflet texture: Leathery, thick, smooth, glabrous and durable. Leaflet color: Upper surface: Glossy, dark green, 139A to 147A, with variable variegation patterns that may be centrally or marginally located. Variegation ranges from yellowish green to ivory: 145A, 150B/150C/150D, and 154C/154D. Leaflets may also be solid green or solid ivory. Lower surface: Slight gloss, green, 147B, with variable variegation patterns that may be centrally or marginally located. Variegation light green, typically 144C. Leaflets may also be solid dark or light green. Venation, upper surface: 147B. Venation, lower surface: Prominent, 144B/144C. Leaf petiole length: About 5 cm. Leaf petiole diameter, at base: About 3 mm. Leaflet petiole length: About 8 mm. Leaflet petiole diameter: About 1 mm. Leaf petiole color: 145A. Leaflet petiole color: Depends on leaflet color, 147A to 150D.

Flower Description: Flowers have not been observed on plants of the new Schefflera.

Disease resistance: No known Schefflera diseases observed to date on plants grown under commercial shadehouse conditions.

It is claimed:

1. A new and distinct cultivar of Schefflera plant named 'PVN II Variegated', as illustrated and described.

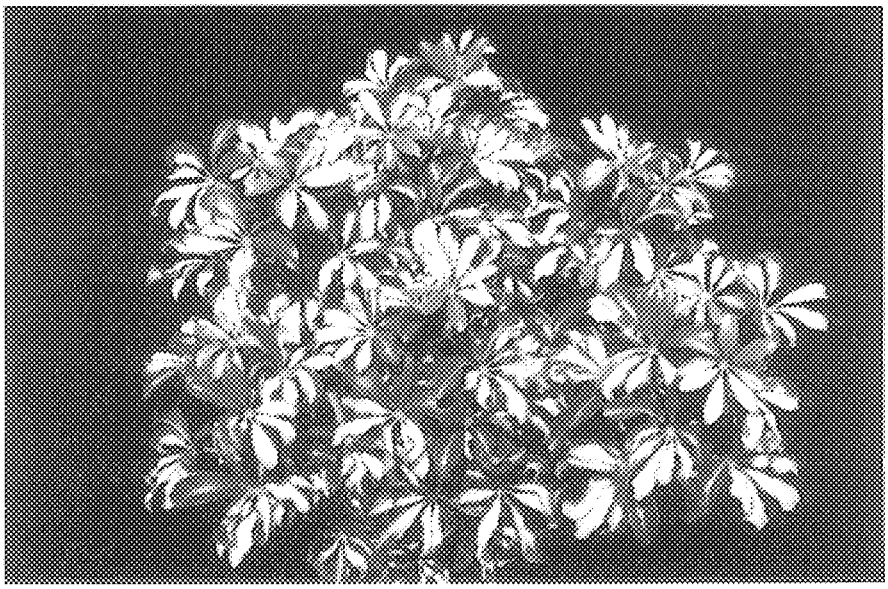
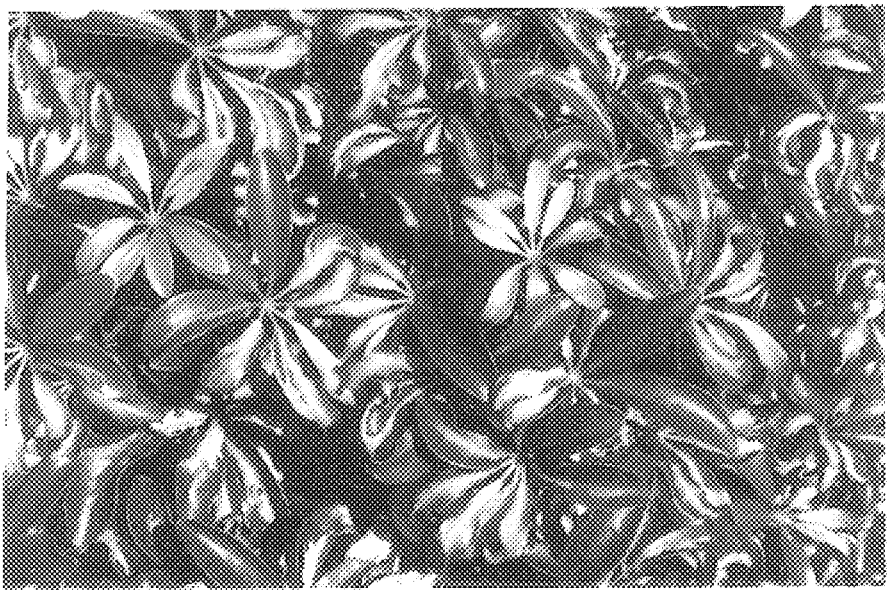

* * * * *